United States Patent
Ferreira et al.

(10) Patent No.: US 10,271,716 B2
(45) Date of Patent: Apr. 30, 2019

(54) ENDOSCOPIC VACUUM CONTROLLER (75) Inventors: Danial P. Ferreira, Milford, CT (US); Christopher A. Battles, Seymour, CT (US)

(73) Assignee: C.R. Bard, Inc., Murray Hill, NJ (US)

(*) Notice: Subject to any disclaimer, the term of this patent is extended or adjusted under 35 U.S.C. 154(b) by 705 days.

(21) Appl. No.: 13/001,127

(22) PCT Filed: Jun. 27, 2008

(86) PCT No.: PCT/US2008/008104
§ 371 (c)(1),
(2), (4) Date: Jun. 28, 2011

(87) PCT Pub. No.: WO2009/157908
PCT Pub. Date: Dec. 30, 2009

(65) Prior Publication Data
US 2011/0251459 A1 Oct. 13, 2011

(51) Int. Cl.
*A61B 1/00* (2006.01)
*A61B 1/015* (2006.01)

(52) U.S. Cl.
CPC .......... *A61B 1/015* (2013.01); *A61B 1/00133* (2013.01); *A61B 1/00128* (2013.01)

(58) Field of Classification Search
CPC .............. A61M 39/284; A61M 1/0025; A61M 1/0027; A61M 1/0029; G01F 23/164; A61B 1/015
(Continued)

(56) References Cited

U.S. PATENT DOCUMENTS 2,850,900 A * 9/1958 Billington ............. F17C 13/025
116/266
3,497,175 A * 2/1970 Koland ............................ 251/9
(Continued)

FOREIGN PATENT DOCUMENTS

| GB | 775476 | 5/1957 |
| JP | 7-39512 | 2/1995 |

(Continued)

OTHER PUBLICATIONS

International Search Report and Written Opinion of the ISA, International application No. PCT/US08/08104, dated Oct. 24, 2008.
(Continued)

*Primary Examiner* — Alexandra L Newton
*Assistant Examiner* — Rynae Boler
(74) *Attorney, Agent, or Firm* — Wolf, Greenfield & Sacks, P.C.

(57) ABSTRACT

An endoscopic vacuum controller may include a housing having a vacuum inlet, a vacuum outlet configured to be coupled to a vacuum source, and a vacuum passage fluidly coupling the vacuum inlet to the vacuum outlet. The vacuum controller may also include an actuator supported by the housing and configured to control the flow of fluid through the vacuum passage. An indicator may be supported by the housing to provide an indication that a predetermined vacuum level is being drawn at the vacuum inlet. The vacuum controller may include a connector to detachably couple the housing to an endoscope shaft. The connector may be configured to slidably couple the housing to the endoscope shaft to allow adjustment of the controller along the length of the shaft while the housing remains coupled to the shaft.

27 Claims, 11 Drawing Sheets (58) Field of Classification Search
USPC .............. 600/156–159; 604/250; 116/272
See application file for complete search history.

(56) References Cited

U.S. PATENT DOCUMENTS

| | | | |
|---|---|---|---|
| 3,612,722 A * | 10/1971 | Neward | 417/63 |
| 3,786,671 A * | 1/1974 | Caron | G01M 3/025 |
| | | | 116/272 |
| 3,911,919 A * | 10/1975 | Raitto | 604/119 |
| 4,146,019 A | 3/1979 | Bass et al. | |
| 4,408,598 A | 10/1983 | Ueda | |
| 4,412,531 A | 11/1983 | Chikashige | |
| 4,519,385 A | 5/1985 | Atkinson et al. | |
| 4,524,802 A | 6/1985 | Lawrence et al. | |
| 4,537,209 A | 8/1985 | Sasa | |
| 4,561,428 A | 12/1985 | Konomura | |
| 4,572,163 A | 2/1986 | Collins et al. | |
| 4,617,015 A * | 10/1986 | Foltz | A61M 16/044 |
| | | | 116/DIG. 9 |
| 4,646,722 A | 3/1987 | Silverstein et al. | |
| 4,662,871 A | 5/1987 | Rafelson | |
| 4,691,738 A | 9/1987 | McCune | |
| 4,735,194 A | 4/1988 | Stiegmann | |
| 4,836,199 A | 6/1989 | Palmer | |
| 4,852,551 A | 8/1989 | Opie et al. | |
| 4,872,579 A | 10/1989 | Palmer | |
| 4,927,428 A | 5/1990 | Richards | |
| 4,973,311 A | 11/1990 | Iwakoshi et al. | |
| 4,982,726 A | 1/1991 | Taira | |
| 5,019,054 A | 5/1991 | Clement et al. | |
| 5,083,561 A | 1/1992 | Russo | |
| 5,117,870 A | 6/1992 | Goodale et al. | |
| 5,147,292 A | 9/1992 | Kullas et al. | |
| 5,201,908 A | 4/1993 | Jones | |
| 5,203,769 A | 4/1993 | Clement et al. | |
| 5,215,522 A | 6/1993 | Page et al. | |
| 5,220,916 A | 6/1993 | Russo | |
| 5,228,646 A | 7/1993 | Raines | |
| 5,230,704 A | 7/1993 | Moberg et al. | |
| 5,250,065 A | 10/1993 | Clement et al. | |
| 5,256,160 A | 10/1993 | Clement | |
| 5,257,773 A | 11/1993 | Yoshimoto et al. | |
| 5,269,768 A | 12/1993 | Cheung | |
| 5,277,177 A | 1/1994 | Page et al. | |
| 5,279,549 A * | 1/1994 | Ranford | 604/34 |
| 5,299,561 A | 4/1994 | Yoshimoto | |
| 5,300,043 A * | 4/1994 | Devlin | A61M 1/0043 |
| | | | 604/250 |
| 5,306,237 A | 4/1994 | Clement et al. | |
| 5,322,263 A | 6/1994 | Yoshimoto et al. | |
| 5,335,671 A | 8/1994 | Clement | |
| 5,338,292 A | 8/1994 | Clement et al. | |
| 5,374,244 A | 12/1994 | Clement et al. | |
| 5,409,013 A | 4/1995 | Clement | |
| 5,447,148 A | 9/1995 | Oneda et al. | |
| 5,462,256 A | 10/1995 | Minick et al. | |
| 5,470,316 A | 11/1995 | Tovey et al. | |
| 5,484,402 A | 1/1996 | Saravia et al. | |
| 5,496,270 A | 3/1996 | Nettekoven | |
| 5,505,210 A | 4/1996 | Clement | |
| 5,518,501 A | 5/1996 | Oneda et al. | |
| 5,554,112 A | 9/1996 | Walbrink et al. | |
| 5,588,634 A | 12/1996 | Nettekoven | |
| 5,611,336 A | 3/1997 | Page et al. | |
| 5,664,564 A | 9/1997 | Palmer | |
| 5,692,729 A | 12/1997 | Harhen | |
| 5,697,888 A * | 12/1997 | Kobayashi et al. | 600/159 |
| 5,840,015 A | 11/1998 | Ogino | |
| 5,855,562 A | 1/1999 | Moore et al. | |
| 5,919,174 A | 7/1999 | Hanson | |
| 5,992,239 A * | 11/1999 | Boehringer | A61M 1/0031 |
| | | | 600/485 |
| 6,126,630 A | 10/2000 | Selig et al. | |
| 6,152,941 A | 11/2000 | Himes et al. | |
| 6,213,970 B1 | 4/2001 | Nelson et al. | |
| 6,227,200 B1 | 5/2001 | Crump et al. | |
| 6,289,726 B1 * | 9/2001 | Ferris | B01D 35/143 |
| | | | 116/266 |
| 6,340,344 B1 | 1/2002 | Christopher | |
| 6,364,853 B1 | 4/2002 | French | |
| 6,383,132 B1 | 5/2002 | Wimmer | |
| 6,419,654 B1 | 7/2002 | Kadan | |
| 6,533,720 B1 | 3/2003 | Dhindsa | |
| 6,585,642 B2 | 7/2003 | Christopher | |
| 6,623,445 B1 | 9/2003 | Nelson et al. | |
| 6,666,818 B2 | 12/2003 | Dhindsa | |
| 6,679,834 B2 | 1/2004 | Stahl et al. | |
| 6,786,865 B2 | 9/2004 | Dhindsa | |
| 6,805,125 B1 | 10/2004 | Crump et al. | |
| 6,811,142 B2 | 11/2004 | Svendsen | |
| 6,824,544 B2 | 11/2004 | Boebel et al. | |
| 6,849,042 B2 | 2/2005 | Christopher | |
| 6,849,043 B2 | 2/2005 | Kondo | |
| 6,875,198 B2 | 4/2005 | Foley | |
| 6,908,429 B2 | 6/2005 | Heimberger | |
| 6,918,902 B2 | 7/2005 | French et al. | |
| 6,923,184 B1 | 8/2005 | Russo | |
| 6,929,602 B2 | 8/2005 | Hirakui et al. | |
| 6,974,466 B2 | 12/2005 | Ahmed et al. | |
| 6,978,783 B2 | 12/2005 | Svendsen | |
| 7,021,313 B1 | 4/2006 | Crump et al. | |
| 7,025,755 B2 | 4/2006 | Epstien | |
| 7,112,207 B2 | 9/2006 | Allen et al. | |
| 7,204,842 B2 | 4/2007 | Geitz | |
| 7,223,230 B2 | 5/2007 | Zirps et al. | |
| 2002/0082568 A1 | 6/2002 | Yam | |
| 2002/0188279 A1 * | 12/2002 | Waddell | A61M 1/0031 |
| | | | 604/540 |
| 2003/0106559 A1 | 6/2003 | Svendsen | |
| 2003/0187467 A1 | 10/2003 | Schreck | |
| 2003/0208209 A1 | 11/2003 | Gambale et al. | |
| 2004/0140444 A1 * | 7/2004 | Beck et al. | 251/142 |
| 2004/0158203 A1 | 8/2004 | Cover et al. | |
| 2004/0182393 A1 | 9/2004 | MacMillan et al. | |
| 2004/0220449 A1 | 11/2004 | Zirps et al. | |
| 2005/0027165 A1 | 2/2005 | Rovegno | |
| 2005/0043745 A1 | 2/2005 | Alferness et al. | |
| 2005/0075600 A1 | 4/2005 | Nelson et al. | |
| 2005/0124966 A1 * | 6/2005 | Karpowicz et al. | 604/500 |
| 2005/0199243 A1 | 9/2005 | Svendsen | |
| 2006/0041190 A1 | 2/2006 | Sato | |
| 2006/0047185 A1 | 3/2006 | Shener et al. | |
| 2006/0063975 A1 | 3/2006 | Hipp et al. | |
| 2006/0100481 A1 | 5/2006 | Soble et al. | |
| 2006/0100485 A1 | 5/2006 | Arai et al. | |
| 2006/0253126 A1 | 11/2006 | Bjerken et al. | |
| 2006/0253127 A1 | 11/2006 | Bjerken | |
| 2007/0016136 A1 | 1/2007 | Opie | |
| 2007/0027359 A1 | 2/2007 | Salman | |
| 2007/0043384 A1 | 2/2007 | Oritiz et al. | |
| 2007/0100324 A1 | 5/2007 | Tempel et al. | |
| 2007/0123824 A1 | 5/2007 | Kavackis | |
| 2008/0200906 A1 * | 8/2008 | Sanders | A61M 1/0001 |
| | | | 604/543 |

FOREIGN PATENT DOCUMENTS

| | | |
|---|---|---|
| JP | 2001-61772 | 3/2001 |
| JP | 2001-231745 | 8/2001 |
| JP | 2001-321888 | 11/2001 |
| WO | WO 2004/021868 A2 | 3/2004 |

OTHER PUBLICATIONS

Extended European Search Report dated Jul. 4, 2014 for European application No. 08779869.0 (6 pages).

* cited by examiner

ENDOSCOPIC VACUUM CONTROLLER

BACKGROUND OF INVENTION

1. Field of Invention

The present invention relates to a vacuum controller for use with an endoscope.

2. Discussion of Related Art

An endoscope is a medical instrument that can be inserted into the body cavity or organ of a patient for performing various surgical procedures. An endoscope may include an optics system to allow a user to view the body cavity or organ. A working or biopsy channel typically extends along the entire length of the endoscope to allow passage of various instruments, and/or tools into a patient.

An endoscope includes an elongated, flexible shaft within which extends the channels and instrumentation. A control handle is conventionally provided at the proximal end of the shaft for holding and manipulating the endoscope through the patient. One or more controls may be provided on the handle for operating various features of the endoscope. One or more ports are conventionally provided on the handle to provide access to the working or biopsy channel.

For some endoscopic surgical procedures, it may be desirable to draw a vacuum in or near the body cavity or organ of the patient. A fluid conduit may be coupled to a vacuum source to draw a vacuum through a channel of the endoscope or through an external tube.

SUMMARY OF INVENTION

In one illustrative embodiment, an endoscopic vacuum controller includes a housing having a vacuum inlet, a vacuum outlet configured to be coupled to a vacuum source, and a vacuum passage fluidly coupling the vacuum inlet to the vacuum outlet. The vacuum controller also includes an actuator supported by the housing and configured to interrupt a flow of fluid through the vacuum passage, and an indicator supported by the housing. The indicator is configured to provide an indication that a predetermined vacuum level is being drawn at the vacuum inlet.

In another illustrative embodiment, an endoscopic vacuum controller includes a housing having a vacuum inlet, a vacuum outlet configured to be coupled to a vacuum source, and a vacuum passage fluidly coupling the vacuum inlet to the vacuum outlet. The vacuum controller also includes an actuator supported by the housing and configured to control the flow of fluid through the vacuum passage from the vacuum inlet to the vacuum outlet, and an indicator supported by the housing. The indicator is configured to provide an indication that a predetermined vacuum level is being drawn at the vacuum inlet. The vacuum controller further includes a connector to detachably couple the housing to an endoscope shaft.

In a further illustrative embodiment, an endoscopic vacuum controller includes a housing having a vacuum inlet, a vacuum outlet configured to be coupled to a vacuum source, and a vacuum passage fluidly coupling the vacuum inlet to the vacuum outlet. The vacuum controller also includes actuation means supported by the housing for interrupting a flow of fluid through the vacuum passage, and indication means supported by the housing for indicating that a predetermined vacuum level is being drawn at the vacuum inlet.

In yet another illustrative embodiment, a method of providing a vacuum in an endoscopic procedure is provided. The method includes an act of (a) detachably connecting an endoscopic vacuum controller to an endoscope shaft, where the vacuum controller includes a housing having a vacuum inlet, a vacuum outlet configured to be coupled to a vacuum source, and a vacuum passage fluidly coupling the vacuum inlet to the vacuum outlet. The method further includes acts of (b) actuating the vacuum controller to draw a vacuum through the vacuum passage from the vacuum inlet to the vacuum outlet, and (c) determining whether a predetermined vacuum level is being drawn within the housing with an indicator supported by the housing.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF DRAWINGS

In the drawings, each identical or nearly identical component that is illustrated in the various figures is represented by a like numeral. For purposes of clarity, not every component may be labeled in every drawing.

Various embodiments of the invention will now be described, by way of example, with reference to the accompanying drawings, in which.

DETAILED DESCRIPTION

The present invention is directed to an endoscopic vacuum controller that facilitates drawing a vacuum during an endoscopic procedure. It should be appreciated that the vacuum controller may be configured in any of numerous ways, and that the present invention is not limited to the particular devices and techniques described below.

The vacuum controller may be configured to be coupled to a vacuum source and may control when a vacuum is drawn during an endoscopic procedure. It may be desirable to draw a vacuum during an endoscopic procedure for a variety of reasons. For example, when suturing tissue, a vacuum may be used to capture the tissue within a suction port of a tissue fastening device. Once the tissue is captured within the suction port, the tissue fastening device may be used to fasten the captured tissue with one or more sutures. In another endoscopic procedure, a vacuum may be drawn to assist in the removal of material from the surgical site. It should be appreciated that the vacuum controller of the present invention is not limited for use with a particular type of endoscopic procedure or device.

The vacuum controller may include a housing having an inlet and an outlet, where the outlet is configured to be coupled to a vacuum source. A vacuum passage may extend through the housing and fluidly couple the vacuum inlet to the vacuum outlet.

The vacuum controller may include an actuator configured to control the flow of fluid through the vacuum passage. As set forth in more detail below, in one embodiment, the actuator may be configured to allow and interrupt the flow of fluid through the passage. The actuator may include a switch that is actuatable between an open or on position to allow a vacuum to be drawn through the vacuum passage and a closed or off position to prevent a vacuum from being drawn through the vacuum passage.

The vacuum controller may include an indicator configured to provide an indication of the vacuum level being drawn through the vacuum passage. In one embodiment, the indicator may be configured to present a visual indication as to whether or not a particular vacuum level is being drawn at the controller inlet. In this respect, the vacuum controller may provide hospital or medical personnel with a ready indication as to when a predetermined vacuum level is reached for performing a surgical procedure. If the predetermined vacuum level has been reached, the user may proceed with the endoscopic procedure. If the predetermined vacuum level has not been reached, the user may wait to perform the procedure.

The amount of vacuum that may be drawn from a vacuum source may vary based on numerous factors. In a hospital setting, a vacuum source may be provided by a wall outlet. The indicator on the vacuum controller may alert the user that the current vacuum level in the vacuum passage is or is not sufficient for a particular endoscopic procedure.

When employed in an endoscopic suturing procedure, the level of vacuum may be indicative of the amount of tissue captured by the suturing device. When the amount of vacuum is below a predetermined vacuum level, it may indicate that the amount of tissue captured by the suturing device is insufficient for continuing with the procedure. The indicator may alert the hospital or medical personnel to delay performing the endoscopic suturing procedure until the predetermined vacuum level is reached.

The vacuum controller may include a connector to detachably couple the vacuum controller to an endoscope shaft. Such an arrangement may facilitate the operation of the vacuum controller and the manipulation of the endoscope by the surgeon or endoscopist. The connector may be configured to slidably couple the vacuum controller to the endoscope shaft to allow adjustment of the vacuum controller along the length of the endoscope shaft while the vacuum controller remains coupled to the endoscope shaft. This may permit the user to more readily adjust the position of the vacuum controller relative to the endoscope shaft during an endoscopic procedure. In one illustrative embodiment, the vacuum controller is clipped onto the exterior of the endoscope shaft. It should be appreciated, however, that the vacuum controller may not include a connector and may thus remain detached from the endoscope shaft.

Turning now to the drawings, it should be appreciated that the drawings illustrate various components and features which may be incorporated into one or more embodiments of the present invention. For simplification, several drawings may illustrate more than one optional feature or component. However, the present invention is not limited to the specific embodiments disclosed in the drawings. It should be recognized that the present invention encompasses one or more embodiments which may include only a portion of the components illustrated in any one figure, and/or may also encompass one or more embodiments combining components illustrated in multiple different drawings, and/or may also encompass one or more embodiments not explicitly disclosed in the drawings.

Figure 1:
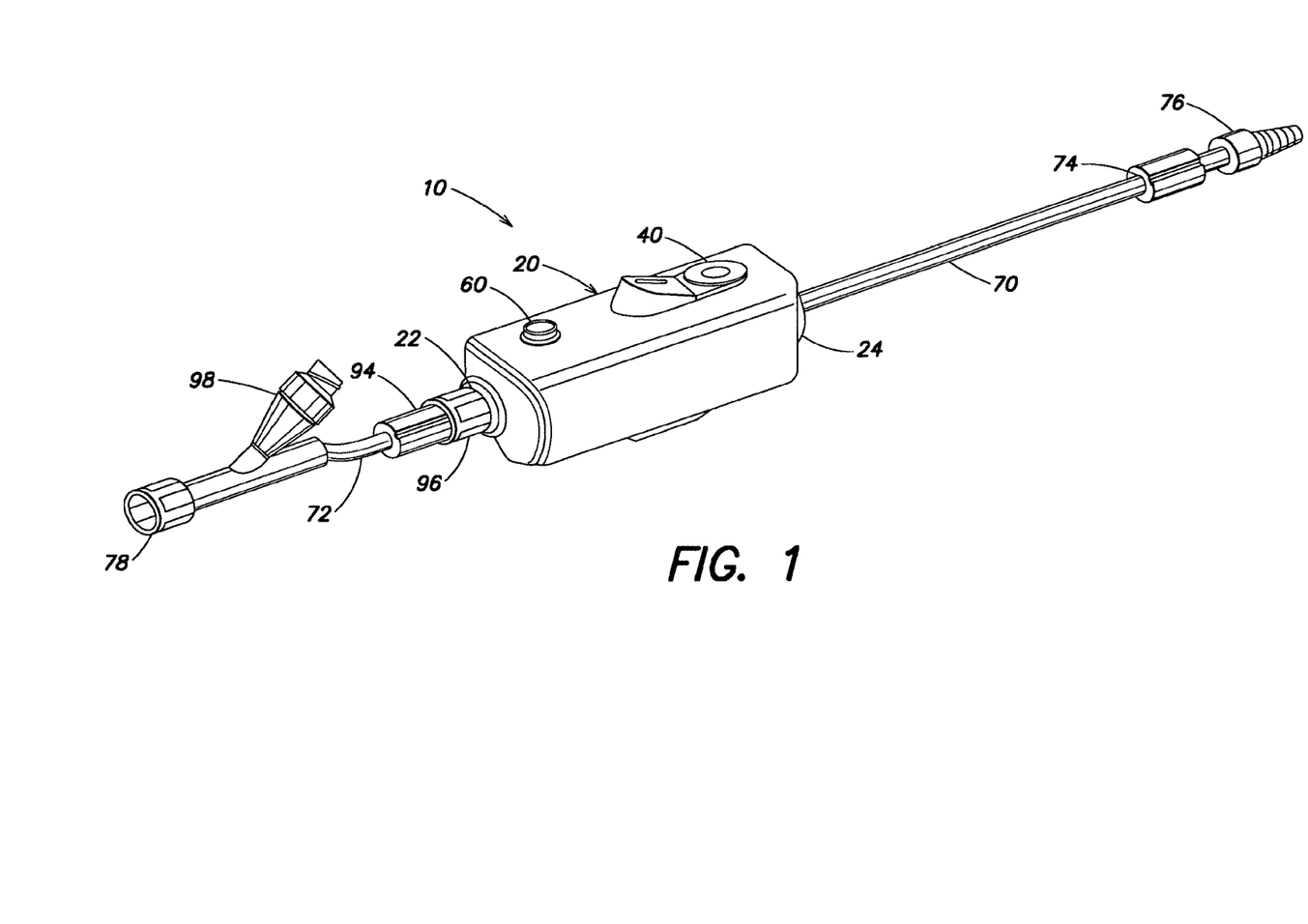
FIG. 1 is perspective view of an endoscopic vacuum controller according to one illustrative embodiment.

FIG. 1 illustrates a perspective view of one embodiment of an endoscopic vacuum controller 10. In this illustrative embodiment, the vacuum controller 10 includes a housing 20 having a vacuum inlet 22 and a vacuum outlet 24 configured to be coupled to a vacuum source (not shown). In one embodiment, the outlet 24 is configured to be coupled to a vacuum source via conduit 70, such as a tube. The inlet 22 may be configured to be coupled to a conduit 72, such as a tube, to draw a vacuum from the vacuum source to the endoscopic tool. In one embodiment, the inlet 22 is configured to draw a vacuum through the vacuum controller 10 and to an endoscopic tool and/or a desired location, such as, for example, near the distal end of an endoscope.

Figure 2:
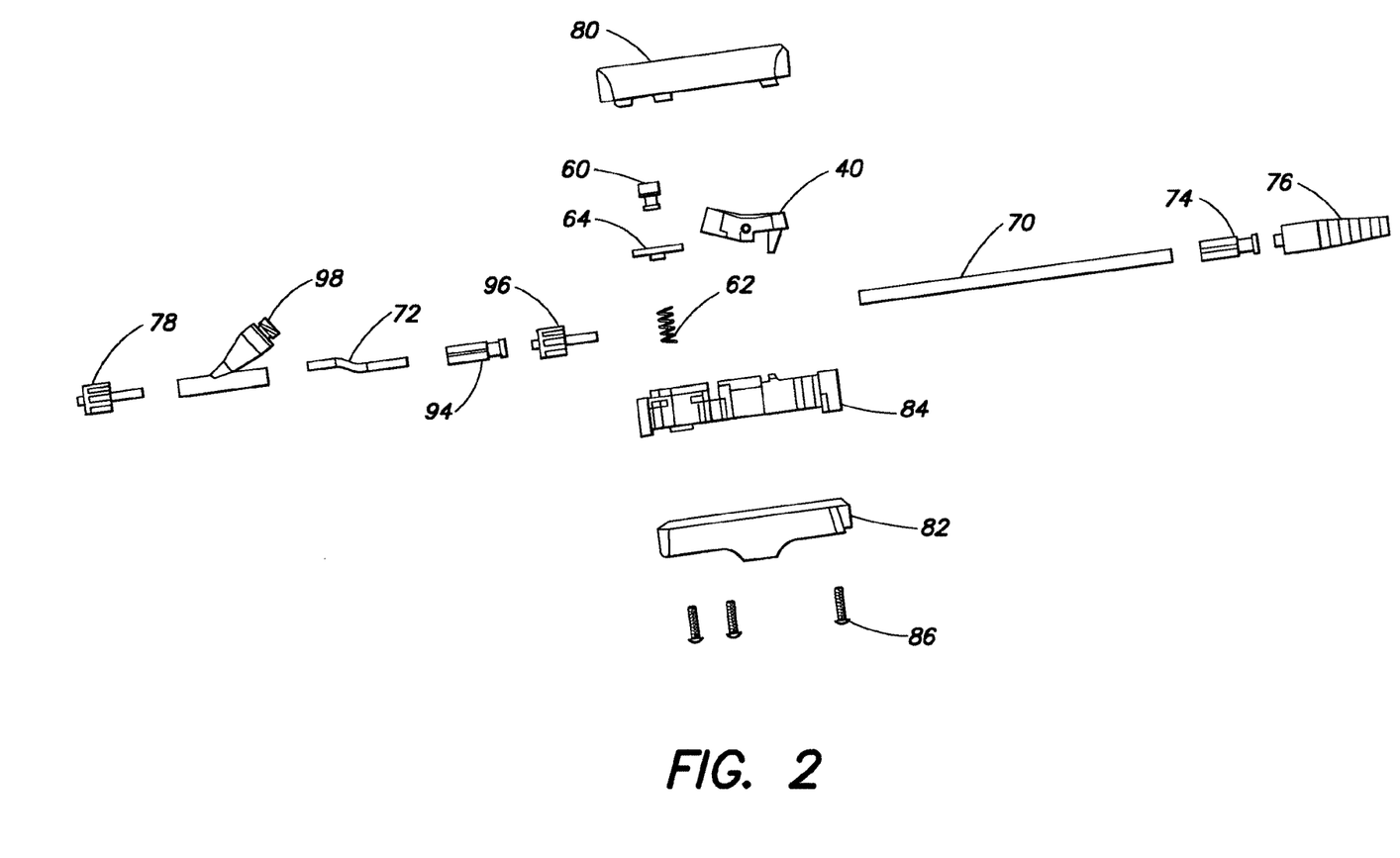
FIG. 2 is an exploded assembly view of the endoscopic vacuum controller of FIG. 1.
Figure 3:
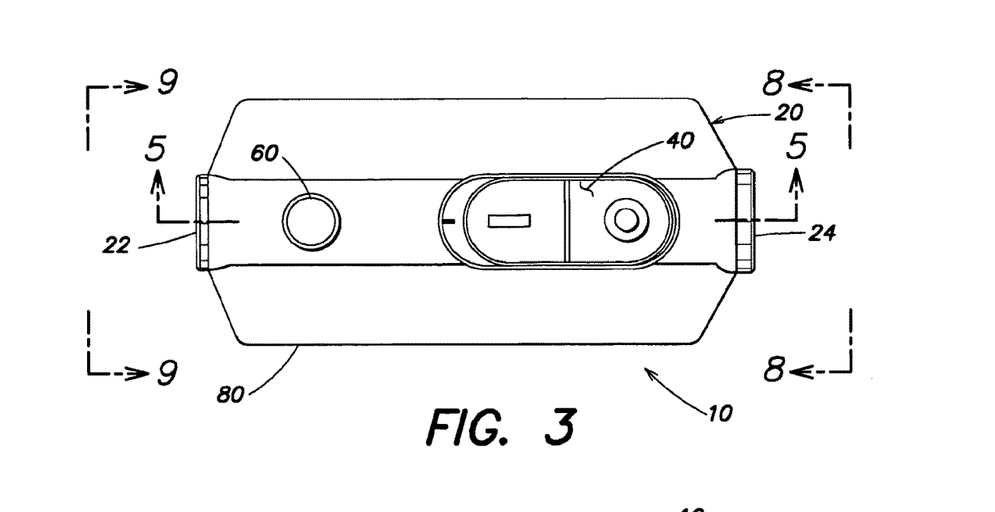
FIG. 3 is a top view of the endoscopic vacuum controller of FIG. 1.
Figure 4:
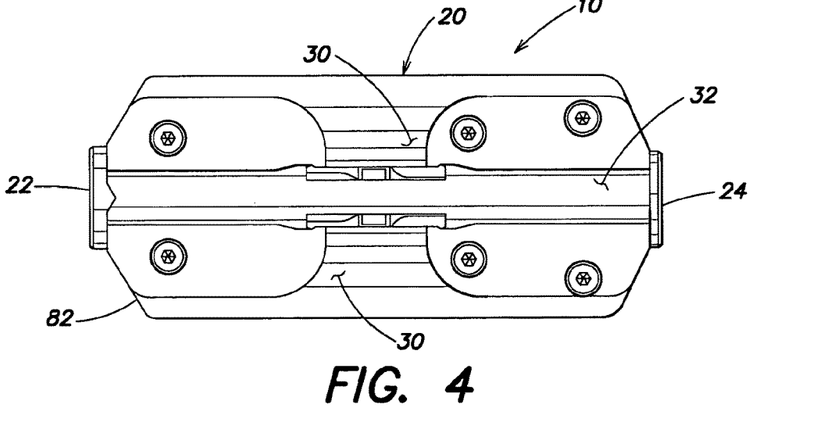
FIG. 4 is a bottom view of the endoscopic vacuum controller of FIG. 1.

The housing 20 includes a passage 26 (see FIGS. 5-7) which fluidly couples the vacuum inlet 22 to the vacuum outlet 24. An actuator 40 is supported by the housing 20 and, as discussed in more detail below, may be configured to control the flow of fluid through the passage 26 from the inlet 22 to the outlet 24. FIG. 2 illustrates an exploded assembly view of the vacuum controller 10 shown in FIG. 1, and FIGS. 3 and 4 illustrate top and bottom views of the vacuum controller 10 according to one embodiment.

Figure 5:
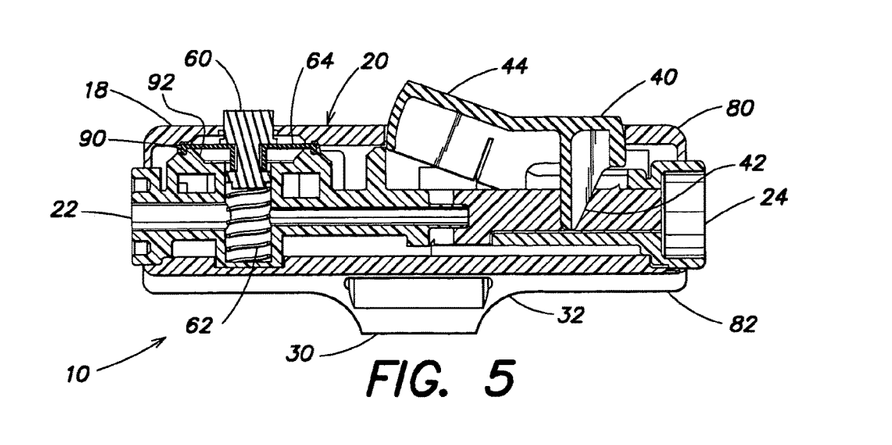
FIG. 5 is a cross-sectional view of the endoscopic vacuum controller taken along line 5-5 shown in FIG. 3.
Figure 6:
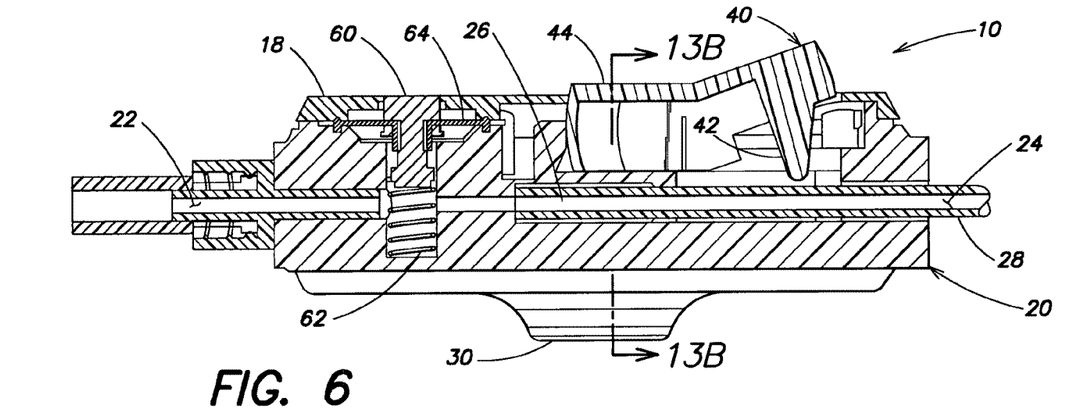
FIG. 6 is a cross-sectional view of an endoscopic vacuum controller with the actuator shown in an open position according to another illustrative embodiment.
Figure 7:
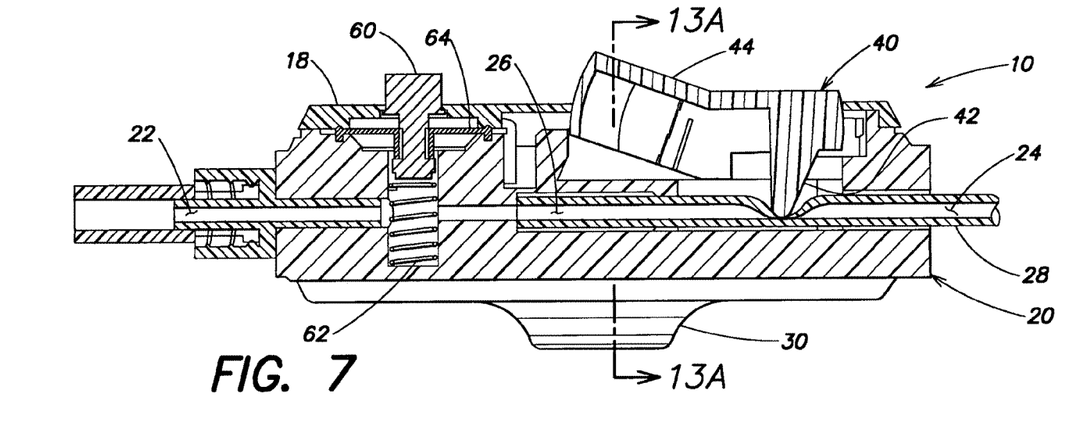
FIG. 7 is a cross-sectional view of the endoscopic vacuum controller shown in FIG. 6 with the actuator shown in a closed position.
Figure 8:
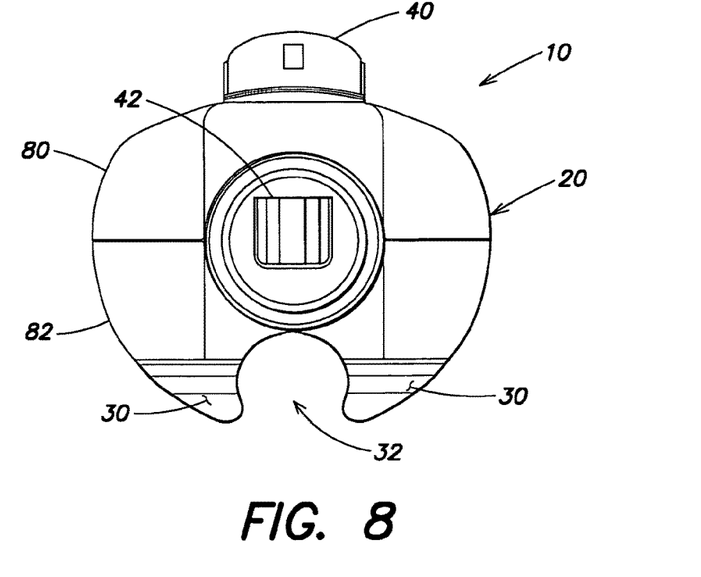
FIG. 8 is a first end view of an endoscopic vacuum controller taken along line 8-8 shown in FIG. 3.
Figure 9:
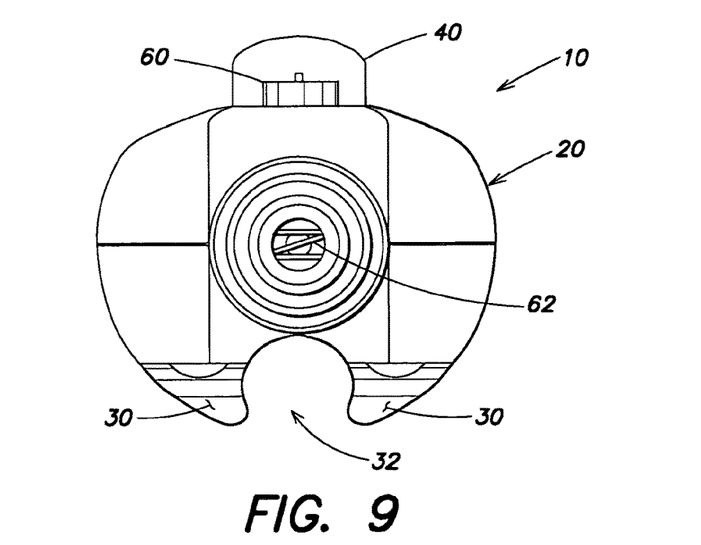
FIG. 9 is a second end view of an endoscopic vacuum controller taken along line 9-9 shown in FIG. 3.
Figure 10:
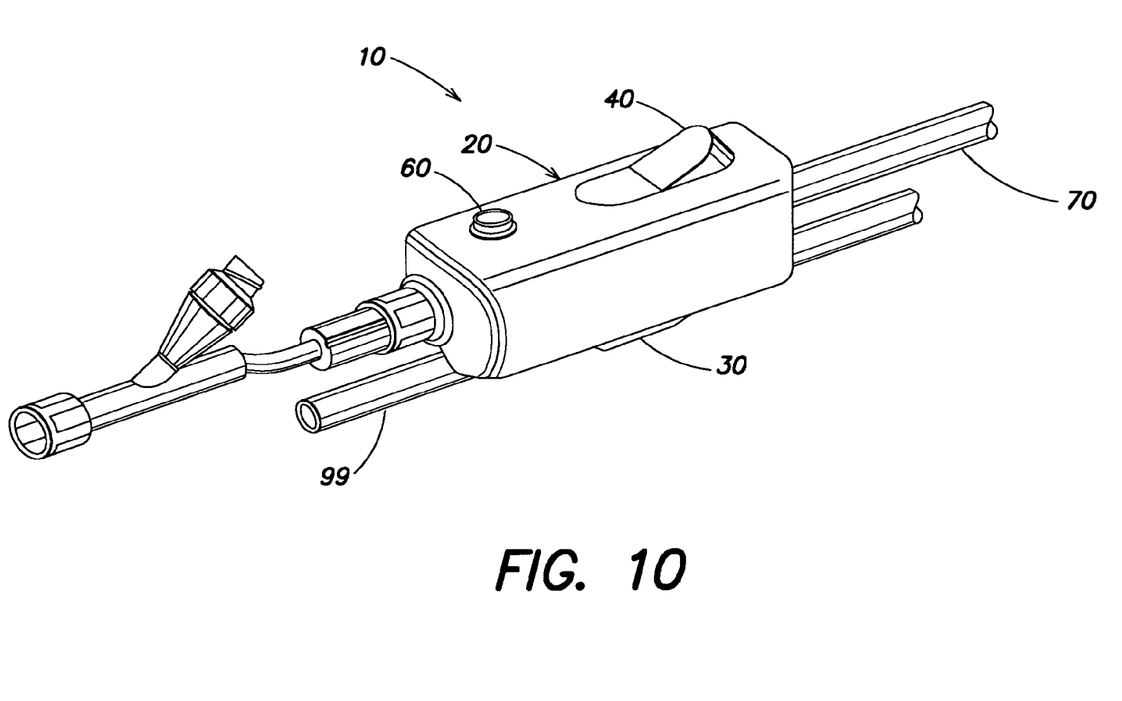
FIG. 10 is a perspective view of an endoscopic vacuum controller of FIG. 1 detachably coupled to an endoscope shaft.

In one embodiment, the actuator 40 is configured to interrupt a flow of fluid, such as air, through the vacuum passage 26. As shown in FIGS. 5-7, in one embodiment, the actuator 40 includes a switch that is actuatable to an open or on position (see FIG. 6) to allow a vacuum to be drawn through the passage 26 and to a closed or off position (see FIGS. 5 and 7) to prevent a vacuum from being drawn through the passage 26. In one illustrative embodiment, the switch includes a protrusion 42 that is arranged to block the passage 26 when actuated to the closed position. The protrusion 42 may include a wedge-shaped rib outwardly extending from the bottom surface of the actuator 40.

As shown in FIGS. 6-7, in one embodiment, at least a portion of the vacuum passage 26 is compressible. In this embodiment, the actuator 40 is arranged to compress a portion of the passage 26, when actuated to a closed position, to block and prevent the flow of fluid through the passage 26. In one illustrative embodiment, a portion of the vacuum passage 26 is formed with a compressible tube 28 which is configured to be compressed by the actuator 40 in the closed position (see FIG. 7). The actuator 40 and the compressible tube 28 may operate similar to a pinch valve.

In one embodiment, the tube 28 may be an integral portion of the conduit 70 configured to couple the fluid outlet 24 of the vacuum controller 10 with the vacuum source. In another embodiment, the tube 28 may be separate from the conduit 70 and the two components may be selectively coupled together.

Figure 12A:
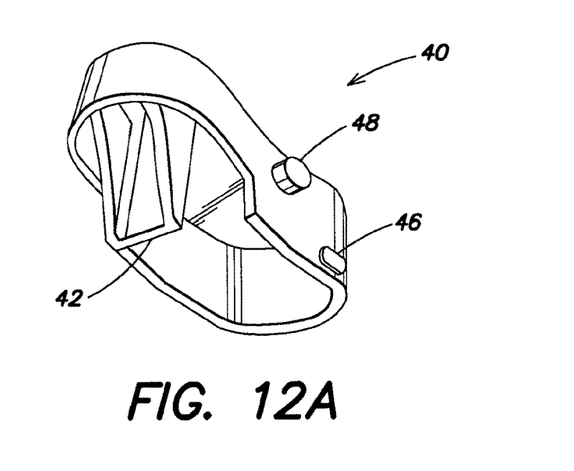
FIGS. 12A-12C illustrate an actuator according to one illustrative embodiment.
Figure 12B:
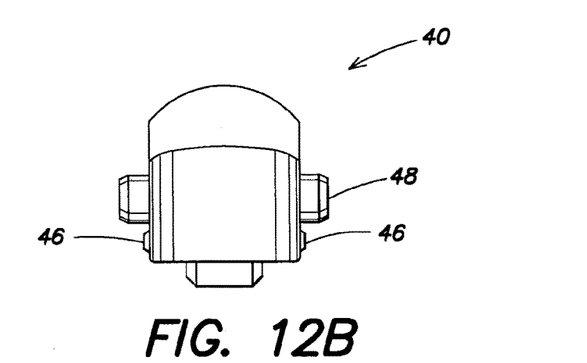
Figure 12C:
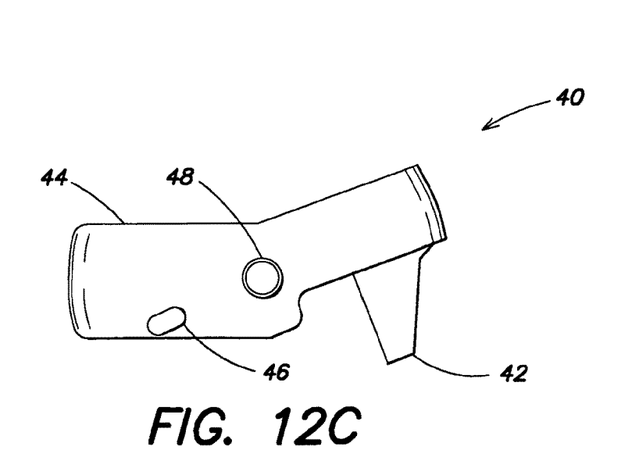

As shown in FIGS. 5-7, the actuator 40 may be pivotally supported by the housing 20 to pivot between an open or on position (see FIG. 6) to a closed or off position (FIGS. 5 and 7). In one embodiment the actuator 40 is configured as a toggle switch and pivots approximately 30° between the open and closed position. In another embodiment, the actuator 40 is configured to pivot approximately 45° between the open and closed position. In another embodiment, it is also contemplated that the actuator 40 may be configured to pivot less than 30° or greater than 45° as the invention is not so limited. As shown in greater detail in FIGS. 12A-12C, in one embodiment, the actuator 40 pivots about an axle 48.

Although the above mentioned embodiments include a pivoting actuator 40, it should be appreciated that the invention is not so limited, as non-pivoting actuators are also contemplated. For example, in one embodiment, the actuator 40 may be supported by the housing 20 and may be configured to move linearly between an open position and a closed position to control the flow of fluid through the vacuum passage 26 from the inlet 22 to the outlet 24.

It should also be appreciated that, in one embodiment, the actuator 40 may be configured to control the flow of fluid through the passage 26 from the inlet 22 to the outlet 24 without interrupting the flow of fluid through the passage 26. For example, the actuator 40 may move between an open position and a partially open position. In the open position, the actuator may be configured to allow a vacuum to be drawn through the passage 26 and in the partially open position, the actuator 40 may be configured to reduce fluid flow through the passage 26.

In one illustrative embodiment, the vacuum controller 10 includes a lock configured to maintain the actuator 40 in the closed position. In this embodiment, the vacuum controller 10 may remain in a closed position, preventing a vacuum from being drawn through the vacuum passage 26, until the user actuates the actuator to its open position. In one embodiment, the user actuates the actuator to an open position to allow a vacuum to be drawn through the passage 26 by manually pressing down on the top surface 44 of the actuator remote from the protrusion 42.

In one embodiment, the vacuum controller 10 may include a lock configured to maintain the actuator in the open position. In this embodiment, the vacuum controller 10 may remain in an open position, allowing a vacuum to be drawn through the vacuum passage 26, until the user actuates the actuator to its closed position.

Figure 13A:
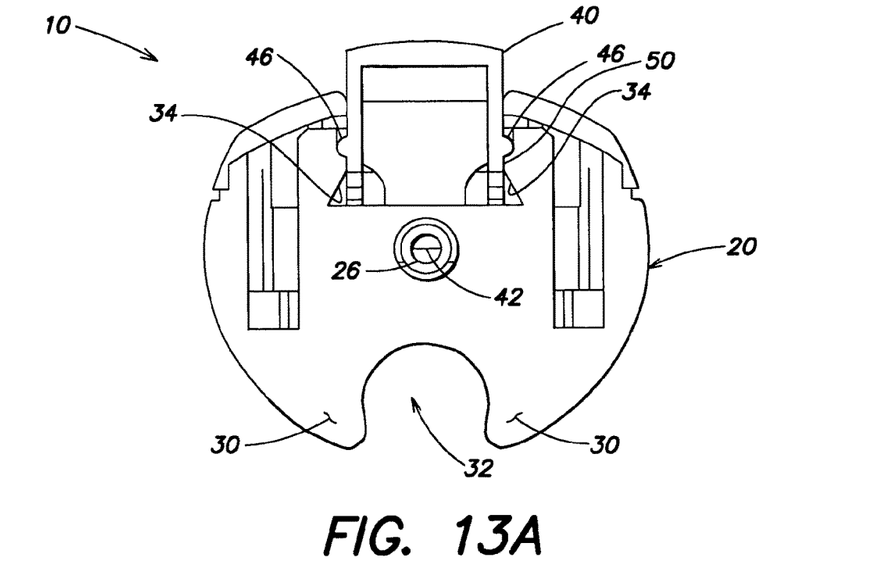
FIGS. 13A-13B illustrate cross-sectional views of the endoscopic vacuum controller taken along line 13A-13A in FIG. 7 and line 13B-13B in FIG. 6.
Figure 13B:
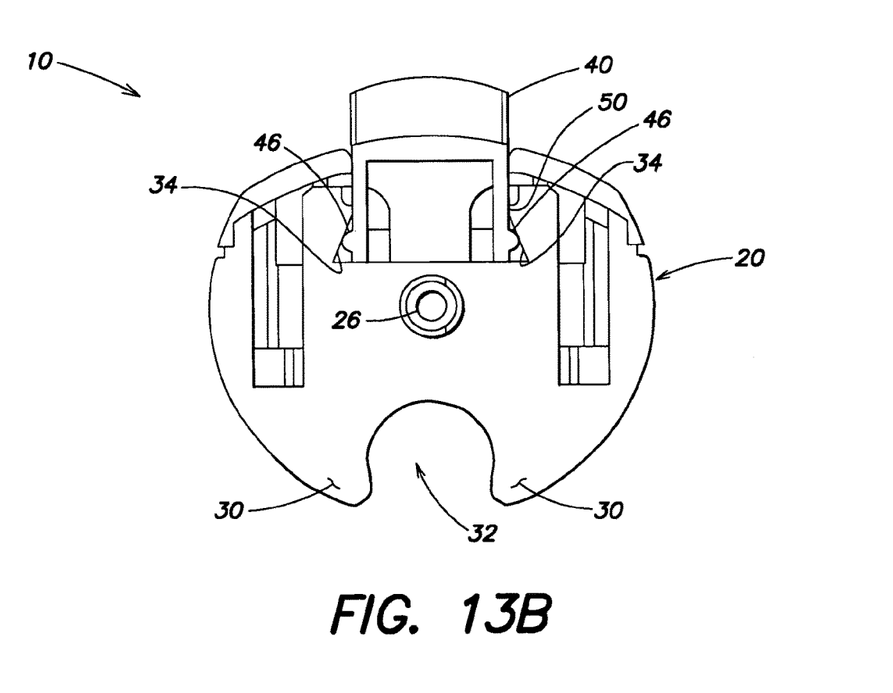

In one illustrative embodiment, the vacuum controller includes a locking detent positioned on at least one of the switch actuator 40 and the housing 20. In the embodiment illustrated in FIGS. 12A-12C and FIGS. 13A-13B, the detent is positioned on the actuator 40. In this embodiment, a pair of detents 46 are provided, one on each side of the actuator 40. As shown in FIGS. 13A-13B, the detents 46 engage a locking feature on the housing 20 to bias the actuator 40 to the closed position. In one illustrative embodiment, the detents 46 engage tapered walls 34 which bias the actuator 40 to the closed position. In another embodiment, the detents 46 may engage one or more ribs formed on the housing 20, as the invention is not limited in this respect.

As mentioned above, in one embodiment, the vacuum passage 26 includes a compressible tube 28 and the actuator 40 may be configured to compress the tube to block the passage 26 in the closed position. When compressed, the tube 28 may exert a force against the actuator 40 that biases the switch 40 toward its open position (see FIG. 6). In one illustrative embodiment shown in FIG. 13A, the detents 46 engage a shelf or flange 50 to counteract the force exerted by the tube 28 against the actuator 40 and maintain the vacuum controller 10 in its closed position.

It should be appreciated that in one embodiment, the detent may be located on the housing 20 and the detent may be configured to engage with a portion of the actuator 40, as the invention is not so limited. Other types of locks apparent to one of ordinary skill in the art are also contemplated by the present invention to maintain the switch actuator in the open position and/or the closed position.

Figure 15A:
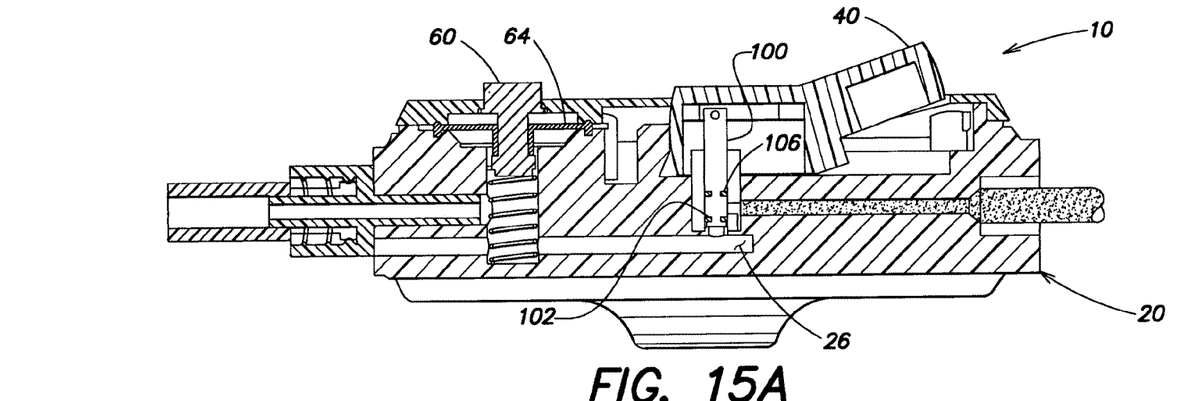
FIGS. 15A-15B illustrate an endoscopic vacuum controller that employs an actuator according to another illustrative embodiment.
Figure 15B:
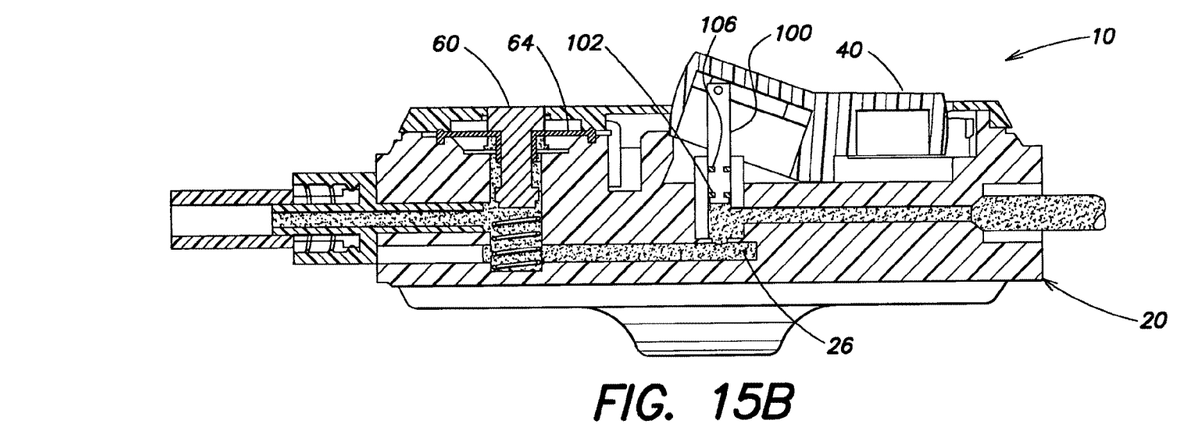

Another illustrative embodiment of an actuator 40 is shown in FIGS. 15A-15B. In this embodiment, the actuator 40 includes a valve arrangement that is configured to extend within the vacuum passage 26. In the illustrative embodiment, the valve includes a valve stem 100 with a sealing member 102 provided on the distal end of the valve stem. The valve stem is coupled to the actuator so that actuation of the actuator moves the valve stem relative to the passage. FIG. 15A illustrates the actuator 40 in a closed position which prevents a vacuum from being drawn through the passage 26. In this embodiment, the valve stem 100 extends into the passage 26 so that the sealing member 102 engages with a portion of the walls of the passage 26 to prevent the flow of fluid through the passage 26.

FIG. 15B illustrates the actuator 40 in an open position to allow a vacuum to be drawn through the vacuum passage 26. In this embodiment, the actuator 40 pivots such that the valve stem 100 and the sealing member 102 do not interfere with the flow of fluid through the vacuum passage 26.

In one embodiment, additional sealing members 106, such as o-rings, are provided to maintain a vacuum within the passage 26. It should be appreciated that in other embodiments, the actuator may be configured differently as the invention is not so limited.

As mentioned above, the vacuum controller 10 may include an indicator 60 supported by the housing 20 that is configured to provide an indication that a predetermined vacuum level is being drawn at the vacuum inlet 22. The predetermined vacuum level may vary based upon the type of endoscopic procedure to be performed. In one embodiment, it may be desirable to achieve a high vacuum level, and approaching the highest vacuum (approximately 29 inHg) may be desirable.

In one embodiment, the predetermined vacuum level is approximately 18 inHg. In another embodiment, the predetermined vacuum level is approximately 20 inHg, and in another embodiment, the predetermined vacuum level is approximately 24 inHg. As discussed in greater detail below, the indicator 60 may be calibrated based upon the desired predetermined vacuum level.

As shown in FIGS. 5-7, in one embodiment, the indicator 60 is biased to a first position relative to the housing 20. The indicator 60 may be movable from the first position to a second position relative to the housing to indicate that the predetermined vacuum level is being drawn at the vacuum inlet 22. In one illustrative embodiment, the indicator 60 may include a pin that is slidably supported by the housing 20 between the first position and the second position. The movement of the indicator from the first position to the second position enables the user to readily determine whether or not a predetermined vacuum level is being drawn at the inlet 22.

In one illustrative embodiment, a spring 62 biases the indicator 60 to the first position. In one illustrative embodiment, the spring 62 is a helical spring which extends into the vacuum passage 26 and is positioned below the indicator 60, such that the indicator 60 rests on the top of the spring 62. It should be appreciated that in other embodiments, other types of springs may be employed.

As shown in FIGS. 5 and 7, in one embodiment, the indicator 60 is configured to protrude outwardly from a surface 18 of the housing 20 in the first position when an insufficient vacuum level is present at the inlet 22. In the embodiment illustrated in FIG. 6, the indicator 60 is configured to be substantially flush with the surface 18 of the housing 20 in the second position to indicate the predetermined vacuum level is being drawn at the vacuum inlet 22. It should be appreciated that in other embodiments, the first and/or second positions of the indicator 60 may differ as the invention is not so limited. For example, in one embodiment, the indicator 60 may be substantially flush with a surface 18 of the housing in the first position, and in the second position, the indicator 60 may be recessed with respect to the surface 18 of the housing 20. In another embodiment, the indicator 60 may protrude outwardly from a surface 18 of the housing in both the first and second position.

Figure 14A:
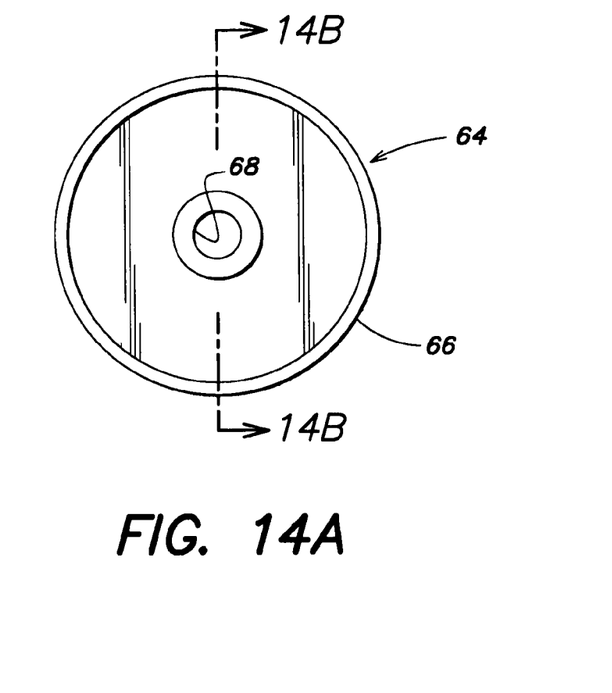
FIGS. 14A-14C illustrate a diaphragm for movably coupling an indicator to the housing of an endoscopic vacuum controller according to one illustrative embodiment.
Figure 14B:
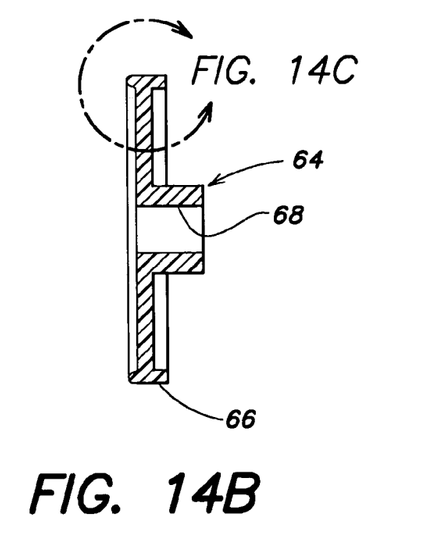
Figure 14C:
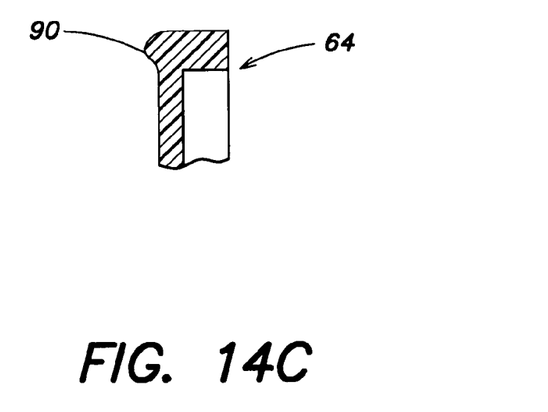

In one illustrative embodiment, the indicator is movably coupled to the housing by a diaphragm 64. One embodiment of a diaphragm is depicted in FIGS. 14A-14C. In this embodiment, the diaphragm 64 has an annular shape with a substantially circular outer diameter 66 configured to be coupled to the housing 20 and a substantially circular inner diameter 68 configured to be coupled to the indicator 60.

The diaphragm 64 may be made of a flexible material such that the diaphragm 64 moves based upon the pressure within the passage 26. If the vacuum controller 10 is disconnected from a vacuum source and/or if the actuator 40 is positioned in a closed position to prevent a vacuum from being drawn through the vacuum passage 26, the pressure within the vacuum passage 26 will be substantially the same as the pressure outside of the housing 20, which may for example be approximately atmospheric pressure. The diaphragm 64 may be configured to be substantially planar in shape when the pressure within the vacuum passage 26 is substantially the same as the pressure outside of the housing 20. When the vacuum controller 10 is coupled to the vacuum source and when the actuator 40 is positioned to allow a vacuum to be drawn through the vacuum passage 26, the diaphragm is drawn inwardly towards the vacuum passage 26 due to the reduced pressure within the vacuum passage 26.

As mentioned above, the indicator 60 may be coupled to the inner diameter 68 of the diaphragm 64 such that the inward movement of the diaphragm 64 also moves the indicator 60 inwardly towards the vacuum passage 26. This movement of the indicator 60 relative to the housing 20 provides an indication of the reduced pressure within the passage 26. In one embodiment, when the vacuum level within the passage 26 reaches a predetermined vacuum level, the diaphragm 64 and indicator 60 move inwardly such that the top of the indicator 60 is flush with a surface 18 of the housing 20.

As shown in FIGS. 5 and 14C, in one embodiment, the diaphragm 64 may include a lip 90 extending about its outer diameter 66. The lip 90 may be configured to engage with portions of the housing 20 to retain the diaphragm 64 within the housing 20. In one embodiment, the housing 20 has a conical relief 92 (see FIG. 5) configured to receive the diaphragm 64 in a nesting arrangement to prevent over stressing the diaphragm 64 as the diaphragm 64 moves inwardly toward the passage 26. One or more seals may be provided to seal the housing 20 and the passage 26 around the indicator 60 and diaphragm 64.

The indicator 60, diaphragm 64 and/or spring 62 may be calibrated based upon the desired predetermined vacuum level at the vacuum inlet 22. In one embodiment the indicator 60, diaphragm 64 and spring 62 are calibrated such that the predetermined vacuum level is between approximately 17-19 inHg. In this respect, the size, shape and materials of the indicator 60, diaphragm 64 and spring 62 may be chosen based upon the level of vacuum needed for a particular endoscopic surgical procedure. For example, variables such as the spring constant of the spring 62, the size and/or diameter of the indicator 60 and the diaphragm material may all affect the movement of the indicator 60 when a vacuum is drawn through the passage 26. The greater the spring constant, the greater the vacuum will be required to move the indicator from the first position to the second position against the resistance of the spring 62. The more flexible the diaphragm 64 material, the less the vacuum will be required to move the indicator 60 from the first position to the second position. The greater the cross-section and/or diameter of the indicator 60, the greater the amount of vacuum will be required to move the indicator 60 from the first position to the second position. The greater the height of the indicator 60 the greater the amount of vacuum will be required to move the indicator inwardly such that the indicator is flush with a surface 18 of the housing 20.

It should be appreciated that a determination of the vacuum level at the inlet 22 may be substantially equal to the vacuum level at the desired vacuum location, such as near the distal end of an endoscope. Because there may be a distance separating the inlet 22 from the desired location for the vacuum, there may a time delay for the two locations to reach an equilibrium such that the vacuum level at the inlet 22 is substantially equal to the vacuum level at the desired location.

Other types of indicators are also contemplated by the present invention. For example, the present invention may include other types of visual indicators, as well as audio indicators. It should be appreciated that the indicator may be made in a variety of ways, as the invention is not limited in this respect.

In one illustrative embodiment, the vacuum controller 10 includes a connector configured to detachably couple the housing 20 to an endoscope shaft. As shown in FIGS. 4-10, the connector may include a pair of rigid arms 30 with a recess 32 formed between the arms to receive at least a portion of an endoscope shaft 99. The size and shape of the recess 32 may vary depending upon the size and shape of the endoscope shaft 99 to which the vacuum controller 10 is to be attached. In the embodiment illustrated in FIGS. 4-10, the connector is integrally formed with the housing 20. It is to be appreciated, however, that the connector may be separately formed and thereafter coupled to the housing 20 in a manner apparent to one of ordinary skill in the art.

In one illustrative embodiment, the recess 32 is substantially C-shaped. It should be appreciated that in other embodiments, the recess 32 may be shaped differently, and may for example be rectangular or irregularly shaped as the invention is not so limited. The recess 32 may be configured to be slightly smaller than the outer diameter of the endoscope shaft to provide an interference fit between the recess 32 and the endoscope shaft 99. In this regard, the endoscope shaft 99 may include a compressible outer covering which may be pinched by the arms and positioned within the recess 30.

During an endoscopic procedure, it may be desirable for a user to adjust the position of the vacuum controller relative to the endoscope shaft. In one embodiment, the connector is configured to slidably couple the housing to an endoscope shaft 99 to allow adjustment of the housing 20 along the length of the shaft while the housing remains coupled to the endoscope shaft. In the illustrative embodiment, the arms 30 are configured to be slidably couple the controller to the endoscope shaft 99 that is positioned within the recess 32.

Figure 11:
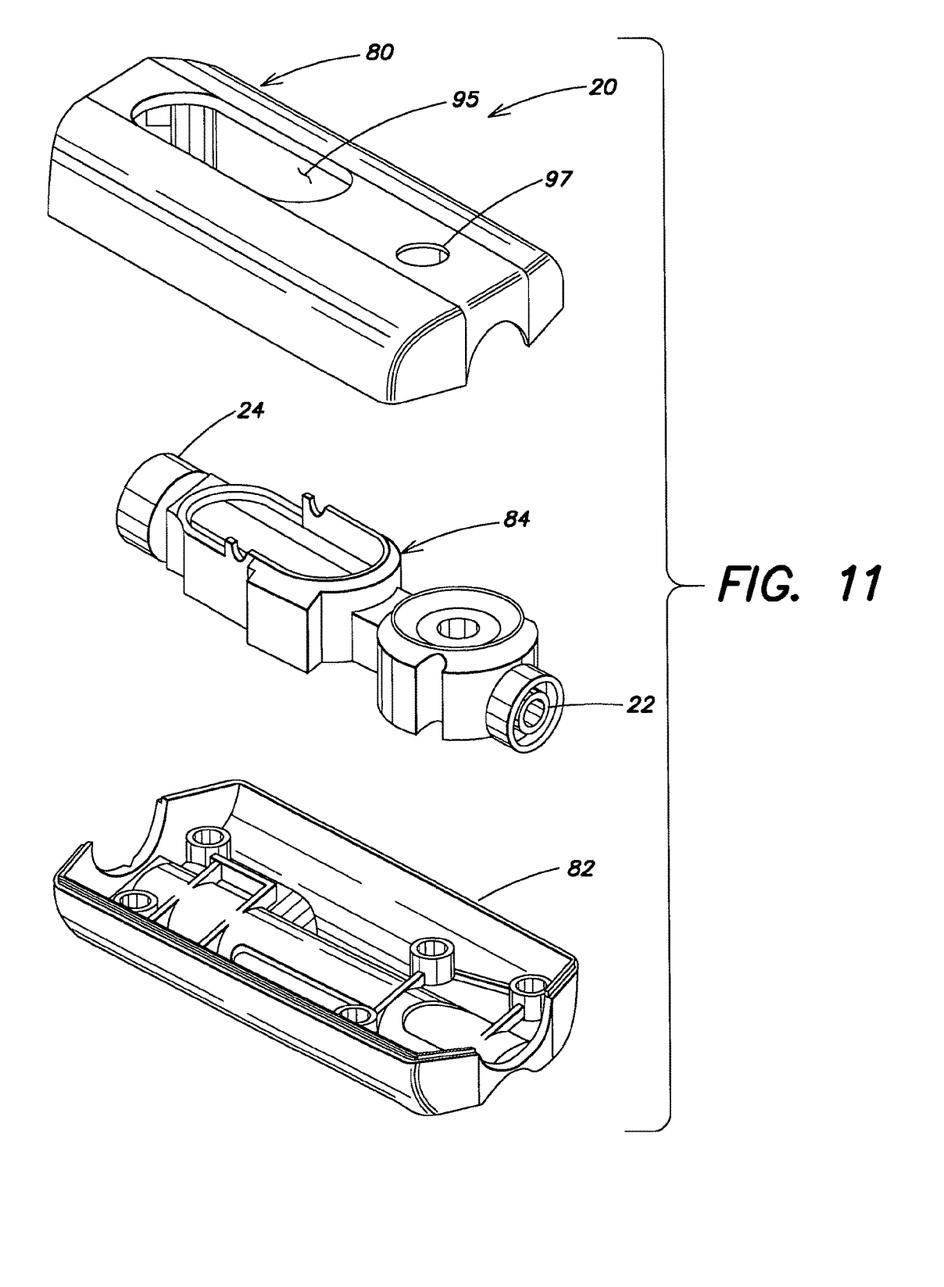
FIG. 11 is an exploded assembly view of an endoscopic vacuum controller housing according to one illustrative embodiment.

As shown in FIG. 11, in one embodiment, the housing 20 includes a top outer shell 80 and a bottom outer shell 82 that enclose an inner housing 84, where the vacuum inlet 22, the vacuum outlet 24 and the vacuum passage 26 are provided with the inner housing 84. In this embodiment, the top outer shell 80 includes a first opening 95 to accommodate the actuator 40 and a second opening 97 to accommodate the indicator 60. In one embodiment, the connector is provided on the bottom outer shell 82 to detachably couple the housing 20 to the endoscope shaft 99. In one embodiment, a plurality of fasteners 86 (see FIG. 2) fasten the top outer shell 80 to the bottom outer shell 82 to enclose the inner housing 84.

Aspects of the present invention are also directed to methods of providing a vacuum in an endoscopic procedure. An endoscopic vacuum controller 10 may be detachably connected to an endoscope shaft 99, where the vacuum controller includes an inlet 22, an outlet 24 and a passage 26 fluidly coupling the inlet and outlet. The vacuum controller may be actuated to draw a vacuum through the passage from the inlet 22 to the outlet 24. A determination of whether a predetermined vacuum level is being drawn at the inlet may be made with an indicator 60 supported by the housing 20. In one embodiment, the vacuum controller may be slid along at least a portion of the length of the endoscope shaft 99 to allow adjustment of the vacuum controller along the length of the shaft.

The types of materials used to manufacture the vacuum controller 10 of the present invention may vary as the invention is not limited in this respect. In one embodiment, the top and bottom outer shell 80, 82 may be made of a polycarbonate plastic and may be configured to ergonomically fit within a user's hand. In one embodiment, the inner housing 84 may be made of a clear polycarbonate so that the compressible tube 28 forming a portion of the vacuum passage 26 may be bonded to the inner housing 84. In one embodiment, the compressible tube 28 is made of a silicone and the tube 28 and the inner housing 84 may be bonded together with a UV curable adhesive. In one embodiment, the tube 28 is formed of a material that is resistant to creeping over time. This may be desirable if the vacuum controller is maintained in the closed position where the protrusion 42 on the actuator 40 may be pressing down on the compressible tube to pinch the vacuum passage 26 closed. The tube 28 may be made of a flexible material that is able to withstand the vacuum levels within the passage 26 without collapsing.

In one embodiment, the indicator 60 is made of an injection molded plastic. The top surface of the indicator 60 may have the same color as the top outer shell 80 and the sides of the indicator may have a different or contrasting color to allow a user to more readily visually determine when the indicator 60 is flush with the top surface 18 of the housing 80 to indicate that a predetermined vacuum level is being drawn at the inlet 22.

In the first position, the indicator 60 may extend out from the top surface 18 of the housing 20 approximately 0.1 inch. In one embodiment, an interference fit may be used between the indicator 60 and the inner diameter 68 of the diaphragm 64. In one embodiment, the outer diameter of the indicator 60 is slightly greater than the inner diameter 68 of the diaphragm 68, and the difference between the two diameters may, for example, be approximately 0.025 inches.

In one embodiment, the diaphragm 64 may be made from a flexible material, such as a silicone, and may have a durometer of approximately 20 A. In one embodiment, the outer diameter 66 of the diaphragm 64 is approximately 0.75 inches and the thickness of the diaphragm is approximately 0.020 inches.

In one embodiment, the spring 62 that biases the indicator 60 to the first position relative to the housing 20 may be a helical spring with a spring rate of approximately 2 lbs/inch. The spring may be fabricated of stainless steel wire having a diameter of approximately 0.016 inches.

As shown in FIGS. 1-2, in one embodiment, additional components may be coupled to the vacuum controller 10 to facilitate drawing a vacuum during an endoscopic procedure. In one embodiment, a female luer 74 and a male luer 76 are provided to couple the outlet conduit 70 to a vacuum source (not shown). Similarly, a female luer 94 and a male luer 96 may be provided to couple the inlet conduit 72 to the vacuum inlet 22 of the housing 20. In one illustrative embodiment, a needleless injection site 98 may be coupled to the conduit 72 with a male luer 78.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An endoscopic vacuum controller comprising: a housing including a fluid inlet, a fluid outlet configured to be coupled to a vacuum source, and a fluid passage fluidly coupling the fluid inlet to the fluid outlet; an actuator supported by the housing, the actuator configured to interrupt fluid flow through the fluid passage in response to actuation by a user; an indicator supported by the housing, the indicator configured to provide an indication that a predetermined vacuum level is being drawn at the fluid inlet, the indicator being movable from a first position to a second position relative to the housing to indicate that the predetermined vacuum level is being drawn at the fluid inlet; and a flexible diaphragm movably coupling the indicator to the housing, the diaphragm constructed and arranged to separate pressure within the housing from pressure outside the housing, the diaphragm having a planar configuration when the pressure within the housing is substantially the same as the pressure outside the housing, the diaphragm having a non-planar configuration in response to a pressure differential on opposing sides of the diaphragm, the indicator being movable in response to the pressure differential on opposing sides of the diaphragm when vacuum is being drawn at the fluid inlet.

2. The vacuum controller of claim 1, wherein the indicator includes a pin slidably supported by the housing between the first position and the second position.

3. The vacuum controller of claim 1, wherein the indicator is biased to the first position relative to the housing, and wherein the indicator is movable from the first position to the second position relative to the housing to indicate that the predetermined vacuum level is being drawn at the fluid inlet.

4. The vacuum controller of claim 3, wherein the indicator protrudes outwardly from a surface of the housing in the first position.

5. The vacuum controller of claim 4, wherein the indicator is retracted and substantially flush with the surface of the housing in the second position.

6. The vacuum controller of claim 1, wherein the diaphragm has an annular configuration.

7. The vacuum controller of claim 6, wherein an outer region of the diaphragm is coupled to the housing and an inner region of the diaphragm is coupled to the indicator.

8. The vacuum controller of claim 1, wherein the diaphragm includes a first surface facing outwardly relative to the housing and a second surface facing inwardly relative to the housing, the indicator protruding beyond the first surface of the diaphragm.

9. The vacuum controller of claim 1, wherein the indicator extends through the diaphragm.

10. The vacuum controller of claim 1, wherein the diaphragm is confined within the housing and the indicator protrudes beyond an exterior surface of the housing when the pressure within the housing is substantially the same as the pressure outside the housing.

11. The vacuum controller of claim 1, wherein the indicator is configured to be positioned at the first position in the absence of a pressure differential between pressure within the housing and pressure outside the housing.

12. The vacuum controller of claim 1, wherein the actuator includes a switch that is manually actuatable to the open position to allow a vacuum to be drawn through the fluid passage and to the closed position to prevent a vacuum from being drawn through the fluid passage.

13. The vacuum controller of claim 12, wherein the switch includes a protrusion that is constructed and arranged to block the fluid passage in the closed position.

14. The vacuum controller of claim 12, wherein at least a portion of the fluid passage is compressible.

15. The vacuum controller of claim 14, wherein the switch is constructed and arranged to compress at least a portion of the fluid passage to block the fluid passage in the closed position.

16. The vacuum controller of claim 15, wherein at least a portion of the fluid passage includes a compressible tube.

17. The vacuum controller of claim 12, wherein the switch is pivotally supported by the housing.

18. The vacuum controller of claim 12, wherein the vacuum controller further comprises: a lock configured to maintain the switch in the closed position.

19. The vacuum controller of claim 18, wherein the lock includes a detent positioned on at least one of the switch and the housing.

20. The vacuum controller of claim 1, wherein the housing includes a connector that is configured to detachably couple the housing to an endoscope shaft.

21. The vacuum controller of claim 20, in combination with an endoscope having an endoscope handle and an endoscope shaft, wherein the connector is mounted to the endoscope shaft.

22. The vacuum controller of claim 20, wherein the connector includes a pair of rigid arms with a recess formed between the rigid arms to receive at least a portion of the endoscope shaft.

23. The vacuum controller of claim 22, wherein the recess is substantially C-shaped.

24. The vacuum controller of claim 20, wherein the connector is configured to slidably couple the housing to the endoscope shaft to allow adjustment of the housing along the length of the endoscope shaft while the housing remains coupled to the endoscope shaft.

25. The vacuum controller of claim 1, wherein the indicator is biased to the first position relative to the housing, and wherein the indicator is movable from the first position to the second position relative to the housing to indicate that the predetermined vacuum level is being drawn at the fluid inlet.

26. The vacuum controller of claim 25, wherein the indicator protrudes outwardly from a surface of the housing in the first position.

27. The vacuum controller of claim 1, wherein the indicator is configured to protrude outside the housing with an outer end surface of the indicator spaced from an external surface of the housing in the first position when a vacuum level less than the predetermined vacuum level is being drawn at the fluid inlet and the indicator is configured to be retracted into the housing with the outer end surface of the indicator being level with or recessed below the external surface of the housing in the second position in response to the predetermined vacuum level being drawn at the fluid inlet.

* * * * *